United States Patent [19]

Payton

[11] Patent Number: 5,049,144

[45] Date of Patent: Sep. 17, 1991

[54] FEMALE URINARY INCONTINENCE APPARATUS

[76] Inventor: Hugh W. Payton, 36 S. Main St., Jeffersonville, Ohio 43128

[21] Appl. No.: 446,910

[22] Filed: Dec. 6, 1989

Related U.S. Application Data

[63] Continuation-in-part of Ser. No. 265,092, Oct. 31, 1988.

[51] Int. Cl.$^5$ ............................................. A61F 5/44
[52] U.S. Cl. .................................. 604/329; 604/331; 128/761
[58] Field of Search ............... 128/760, 761, 762, 764, 128/767, 769, 772, 773, 833–840, 883, 884; 600/29, 31; 604/14, 15, 28, 280, 355, 328–331

[56] References Cited

U.S. PATENT DOCUMENTS

| | | | |
|---|---|---|---|
| 1,033,808 | 7/1912 | Kutch | 604/331 |
| 3,116,734 | 6/1961 | Terman | 604/329 |
| 3,528,423 | 9/1970 | Lee | 128/295 |
| 3,592,197 | 7/1971 | Cohen | 604/280 |
| 3,661,155 | 5/1972 | Lindan | 128/295 |
| 3,722,503 | 3/1973 | Hovick | 128/2 F |
| 3,815,581 | 6/1974 | Levin | 128/2 F |
| 3,995,329 | 12/1976 | Williams | 4/110 |
| 4,023,216 | 5/1977 | Li | 4/110 |
| 4,023,560 | 5/1977 | Cade et al. | 128/2 F |
| 4,116,197 | 9/1978 | Bermingham | 128/286 |
| 4,139,006 | 2/1979 | Corey | 128/127 |
| 4,194,508 | 3/1980 | Andersen | 128/295 |
| 4,246,901 | 1/1981 | Michaud | 128/295 |
| 4,421,511 | 12/1983 | Steer et al. | 604/329 |
| 4,484,917 | 11/1984 | Blackman | 604/327 |
| 4,496,355 | 1/1985 | Hall et al. | 604/327 |
| 4,531,245 | 7/1985 | Loud et al. | 4/144.3 |
| 4,563,183 | 1/1986 | Barrodale et al. | 604/329 |
| 4,568,339 | 2/1986 | Steer | 604/329 |
| 4,583,983 | 4/1986 | Einhorn et al. | 604/329 |
| 4,799,928 | 1/1989 | Crowley | 604/329 |
| 4,886,508 | 12/1989 | Washington | 604/335 |

*Primary Examiner*—Randy C. Shay
*Attorney, Agent, or Firm*—Biebel & French

[57] ABSTRACT

Pubovaginal appliances for the collection of urine from women suffering from incontinence includes a pad configured to engage the pubic region. A bifurcated support body extends posteriorly along the contour of the perineum and terminates in a pair of flexible rods which are bent or carried anteriorly and which diverge caudally. Each rod carries a cylinder or insert proportioned to be received together in the vaginal cavity and are biased by the rods toward the pad to provide a self-holding force for the appliance between the pubis and vagina. A urine deflecting hood and collection cup are carried on the body at the opening formed by the bifurcation, and the hood is urged into contact with the wearer. Two embodiments are described. One has a funnel adopted for connection to a collection bag and the other has an access door for insertion and removal of absorbent material.

8 Claims, 7 Drawing Sheets

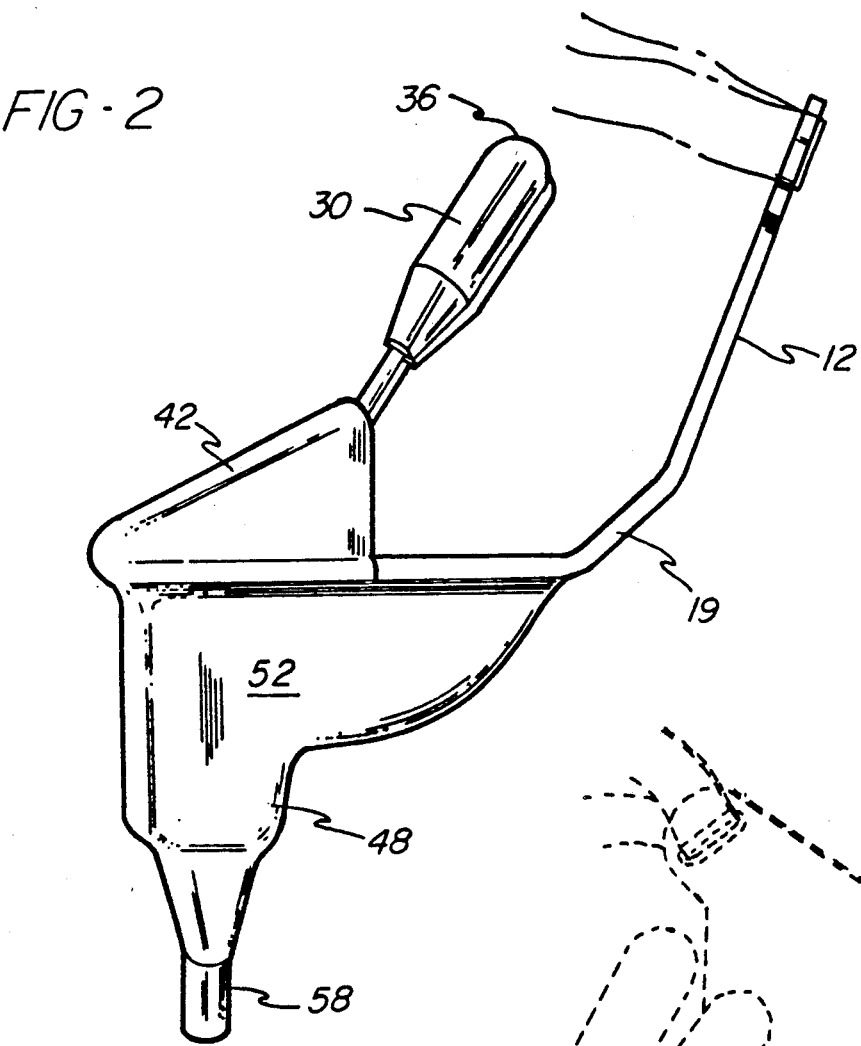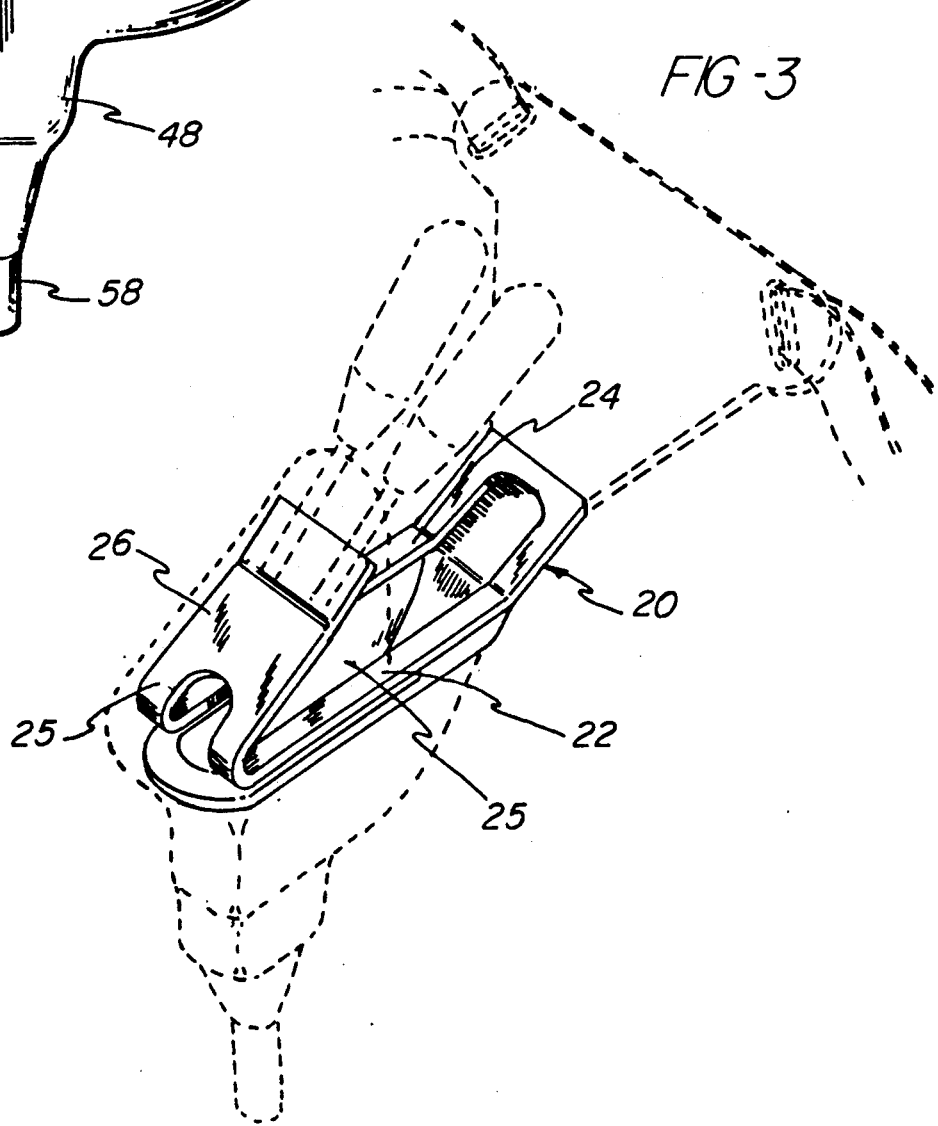

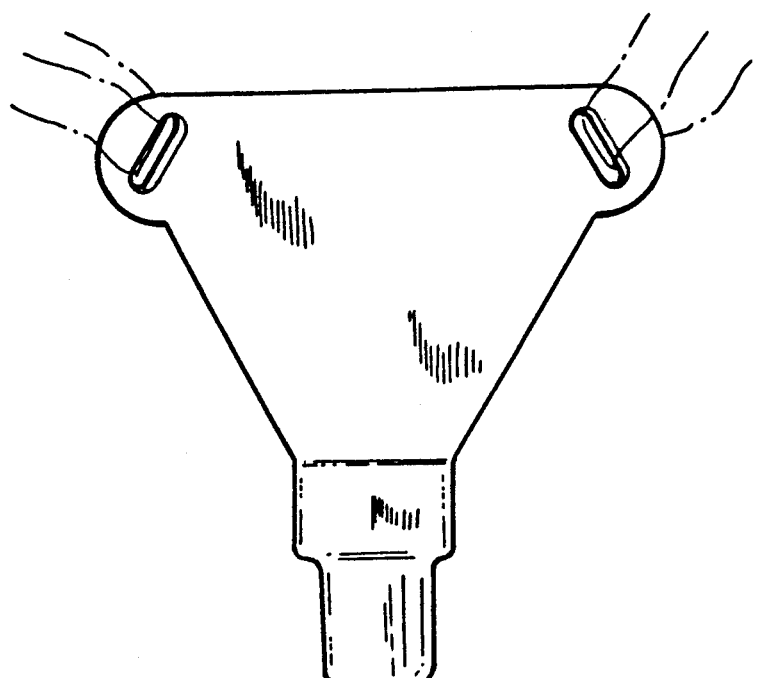
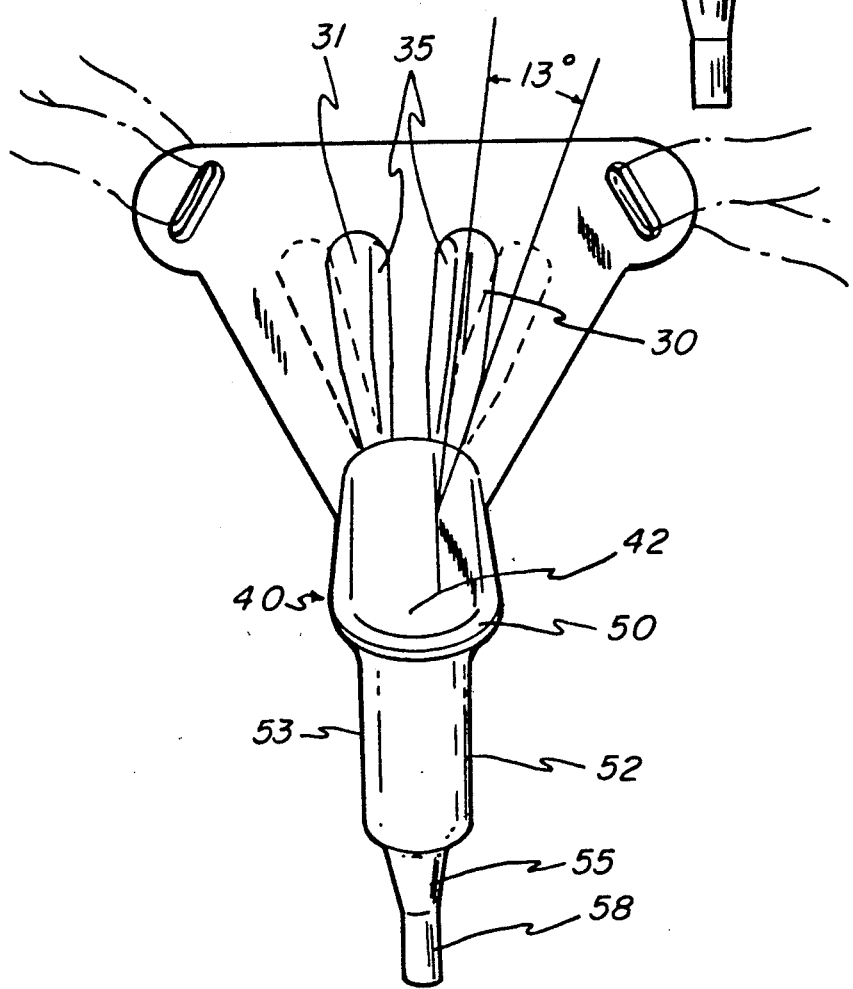

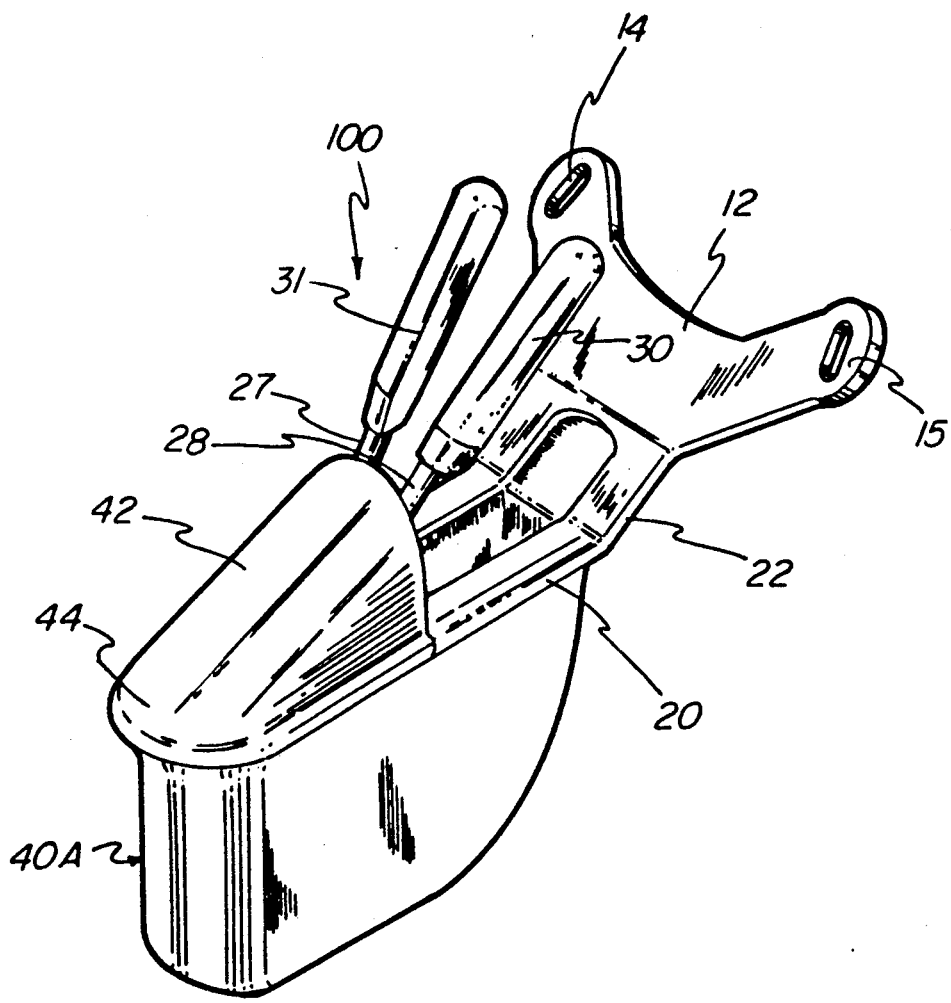

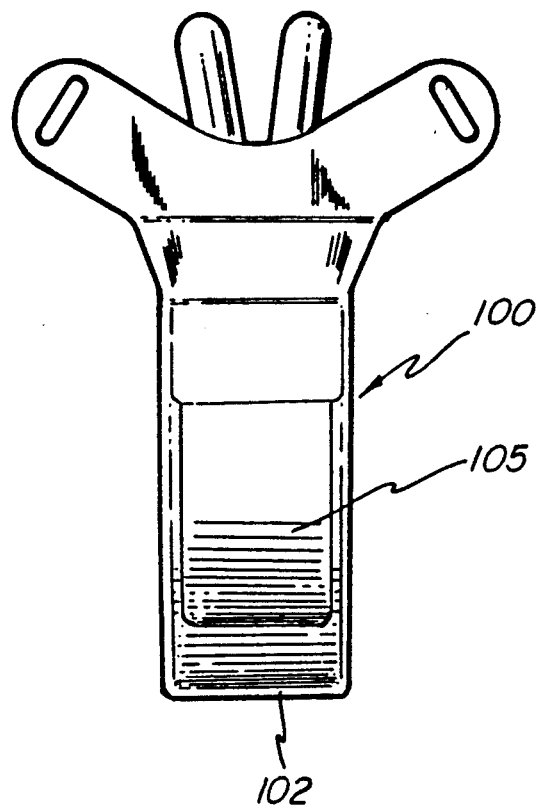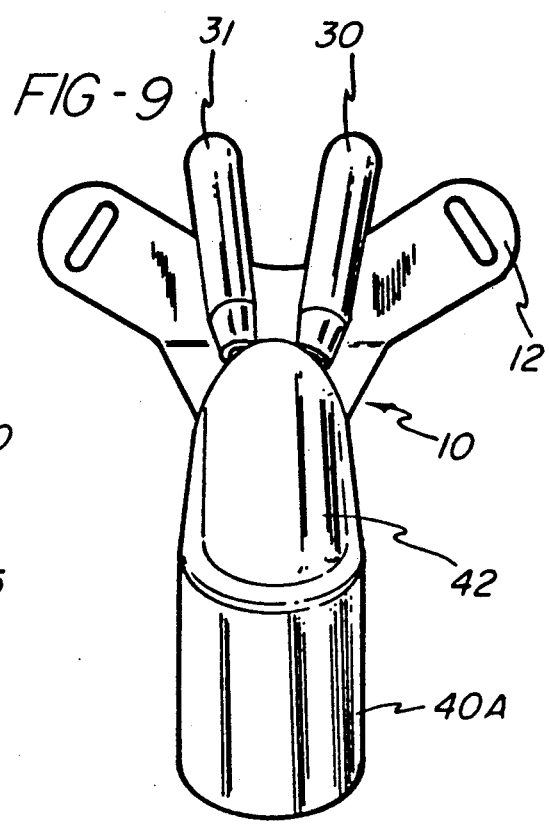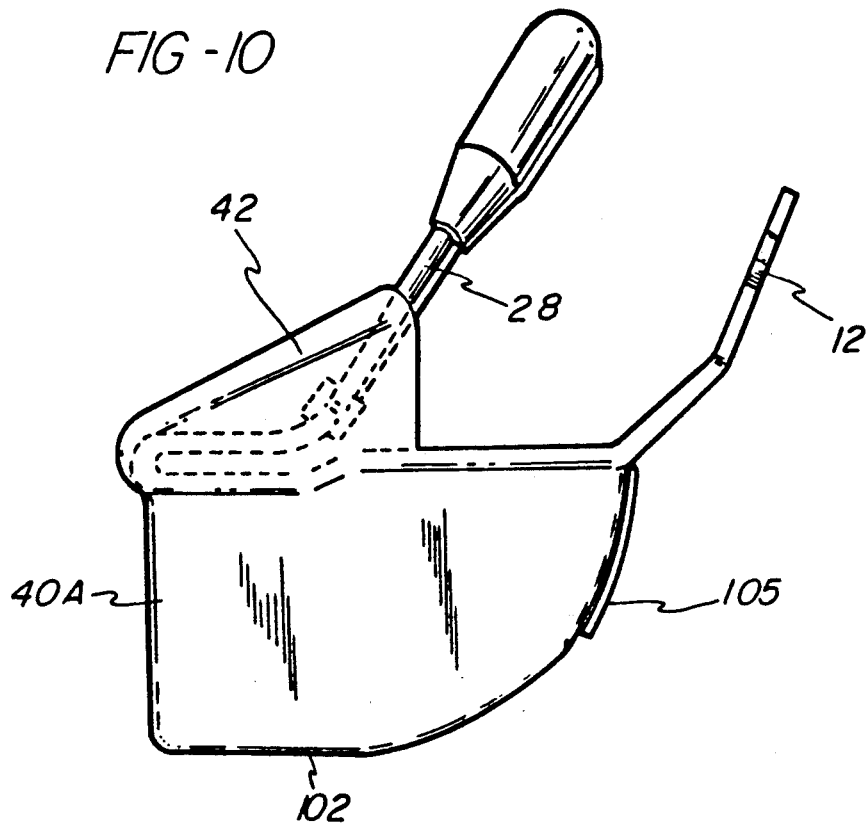

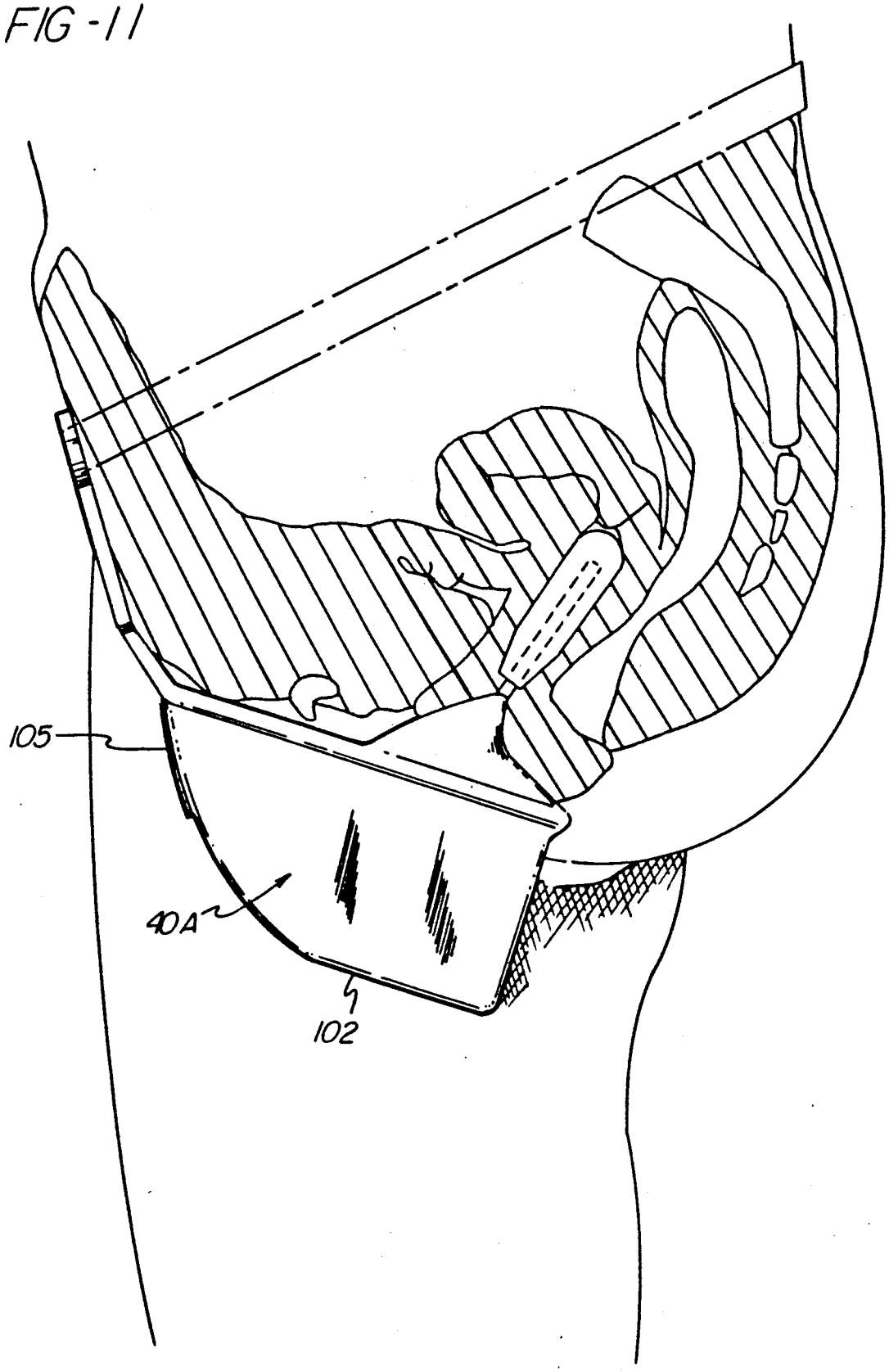

FEMALE URINARY INCONTINENCE APPARATUS

RELATED APPLICATION

This application is a continuation-in-part of application Ser. No. 265,092 filed Oct. 31, 1988.

BACKGROUND OF THE INVENTION

Many post-delivery women suffer from urinary incontinence. This may be aggravated by stressful maneuvers such as coughing, sneezing or any event that increases intra-abdominal pressure. This pressure is transmitted to the bladder, which in the event of inadequate sphincter continuity, results in urinary incontinence. Besides anatomical disorders, any compromise in the nerve supply to the bladder or bladder sphincters will also frequently lead to urinary incontinence. Also, other less common disease states contribute to the overall problem.

Current clinical approaches to cope with the problem in women includes diapers, sanitary napkins, and of course, the indwelling catheter which is usually shunned for multiple reasons. Actually, there is no satisfactory available approach to this embarrassing female inconvenience.

A particularly acute and costly problem exists in patient care for elderly patients in nursing homes and the like. Many elderly women who are confined to nursing home also suffer from urinary incontinence, and since they frequently spend a good deal of time reclining or sitting, gravity-assisted collection devices are of less value. Adult diapers have become the major patient care appliance, and are used in great numbers and accordingly frequently present a correspondingly great disposal problem.

SUMMARY OF THE INVENTION

The invention presented herein provides alternative devices that will appeal to some females. The appliances include a forward pad adapted to be supported against the pubis and a body which follows the contour of the perineum. The body is split or bifurcated and terminates in a pair of forwardly-bent rods. A pair of generally cylinder-shaped insert elements are attached to or supported on the rod ends in side-by-side relation and are urged by the rods transversely or caudally. The cylinder inserts are movable by flexing the rods both anteriorly and caudally, so that the inserts may inter the vagina and proceed anteriorly to the front wall of the vagina. As the parallel inserts enter the vagina, they coalesce to form a rectangle, then spread apart under the influence of the support bars. To aid this process, the inserts may be flat on the adjacent inside opposed surfaces.

The appliance is the self-holding in place following insertion. A urine collection hood and funnel are supported on the body in the space between the bifurcated sections, and formed of soft plastic material, such as medical grade vinyl. In one embodiment the collection hood leads to the collection cup, and is formed of soft and compliant material, and is positioned to collect urine from the urethra. The soft plastic parts comfortably conform to the adjacent body parts, which the inserts are biased outwardly away from each other and anteriorly.

The arrangement of the inserts on the support rods, in combination with the front pad, provides broad internal and external support for the appliance, to permit comfortable retention. The collected urine may be conducted to a conventional thigh-supported collection bag.

In another form of the invention, the collection cup is provided with an access opening in the form of a flap or trap door. The cup is formed of sufficient internal volume so as hold a high absorbent material. For example, high absorbent starch-containing polymeric compositions known as polyacrylonitril, and made in accordance with U.S. Pat. Nos. 3,997,484 and 3,981,100 may be effectively contained and used. Such compositions can absorb up to 50 times their weight in urine. The appliance cup may be closed at the bottom and at the sides, and opened or accessible through the flap for the insertion or removal of such highly absorbent material for proper disposal when saturated.

An object of the invention is the provision of a pubovaginal appliance for collecting urine.

Another object of the invention is the provision of an appliance, as outlined above, in which vaginal insert cylinders are carried on flexible rods extending from a bifurcated support body, which inserts may be coalesced together for insertion, and which then spread apart to form abroad base of support for the appliance.

A further object of the invention is the provision of an appliance, as outlined above, in which a hood and collection portion are carried on a split or bifurcated body portion, and supported by a pair of vaginal inserts carried in side-by-side relation on the distal ends of a pair of rods extending from a rearward part of the body, and by a pubis-engaging front pad carried on a forward part of the body.

A further object of the invention is the provision of an appliance, as outlined above, formed with collection cup means, in which the cup means is formed or provided with an access opening or closable panel or trap door portion, and which cup means is proportioned to receive an adequate quantity of urine absorbent material.

Other objects and advantages of the invention will be apparent form the following description, the accompanying drawings and the appended claims.

BRIEF DESCRIPTION OF DRAWINGS

FIG. 2 is a side elevation thereof;

FIG. 3 is a perspective view, partially in phantom, showing the bifurcated support body in solid lines;

FIG. 4 is a front view of the appliance;

FIG. 5 is a rear view, further illustrating the range of transverse movement of the insert cylinders;

FIG. 7 is a perspective view, similar to FIG. 1, of a modified form of the invention;

FIG. 8 is a front view of the appliance of FIG. 7;

FIG. 9 is an anterior or rear view of the appliance;

FIG. 10 is a side elevation thereof; and

FIG. 11 is a view similar to FIG. 6 showing the anatomical placement of the appliance.

DESCRIPTION OF PREFERRED EMBODIMENTS

Figure 1:
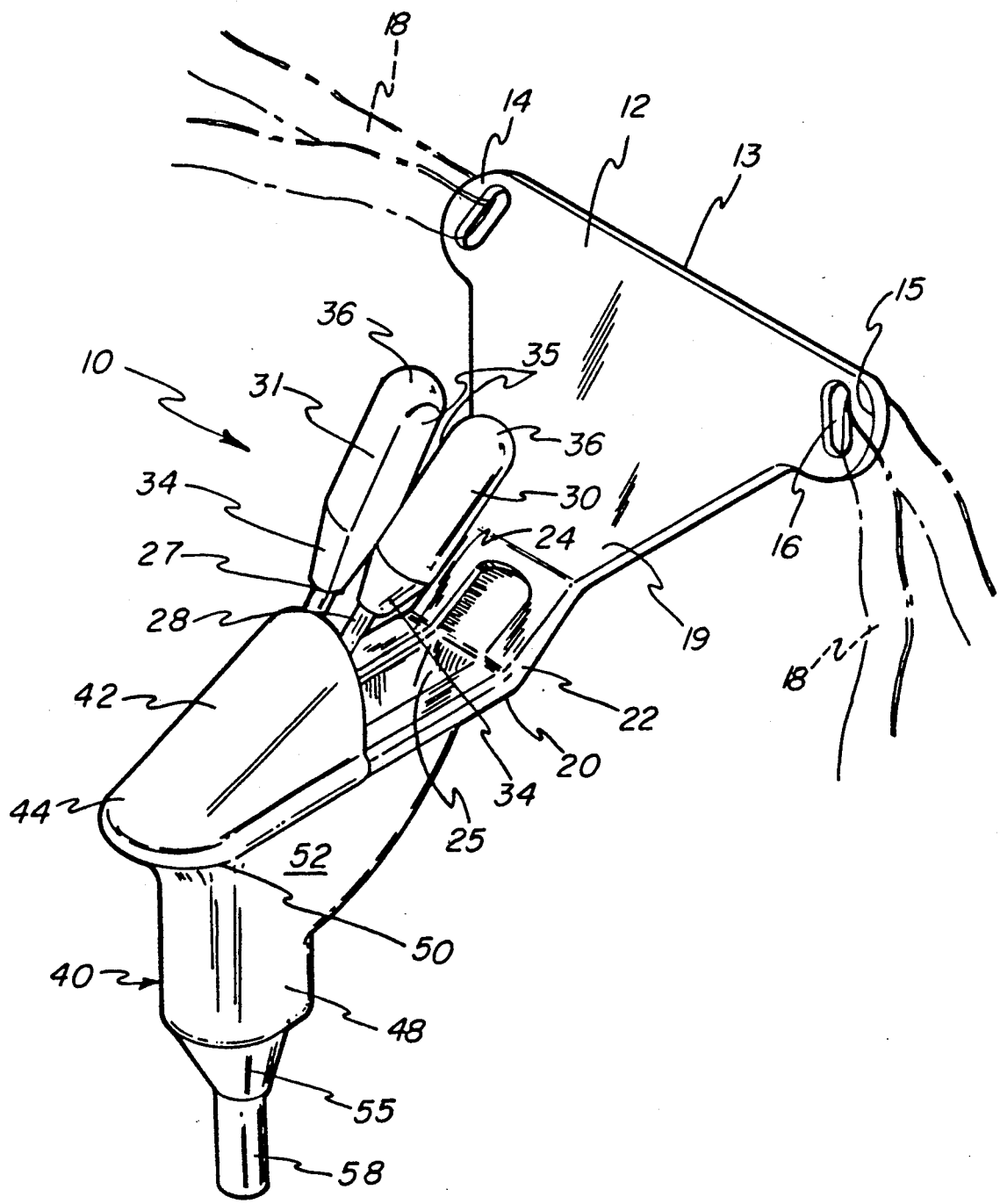
FIG. 1 is a perspective view of one embodiment of the appliance of this invention.

Referring to the drawings, which illustrate preferred embodiments of the invention, an appliance constructed according to one embodiment of this invention is illustrated generally a 10 in FIG. 1 as including a generally triangularly shaped support pad 12 which has its base 13 at the top. The extreme top corners 14 and 15 are formed with slots 16 to receive a waist belt 18. The pad 12 may be formed of relatively firm, thin material to conform to the pubic region.

The lower end 19 of the pad extends posteriorly and is contoured to conform to the perineum region. This lower end forms a more rigid body 20, as shown in full lines in FIG. 3, which is bifurcated or split into a right arm 22 and a left arm 24, and defines an elongated space 25 therebetween. The body has a rear or posterior non-bifurcated portion 26 which is folded partially back upon itself, to form a flexible hinge portion 25.

A pair of flexible rods 27 and 28 extend generally upwardly from the terminal end of the portion 26, and support on their distal ends a pair of cylinder-like bulbs or inserts 30 and 31. The lower ends of the rods are firmly attached to the portion 26.

The inserts 30, 31 each have the same outer contour, and are rounded in the general shape of a cylinder with a tapered or conical bottom 34, at the point of attachment to the rods. The opposed inside surfaces 35 are flat so that when the inserts 30, 31, which are normally held slightly apart by the rods, are brought together, they coalesce effectively into a single object, for ease of insertion. The inserts 30, 31 are formed with smoothly rounded outer ends 36. The rods 27 and 28 urge the inserts transversely apart with a motion as shown by the phantom or broken lines in FIG. 5.

A combination hood and collection cup or funnel 40 is formed in the space 25 and encloses the body 20 about the arms 22 and 24, and the forward portion 26 and hinge 25. The combination hood and collection funnel 40 is formed of a soft and compliant material, such as medical grade vinyl.

The combination includes a hood portion 42 which encloses the rearward part of the body 20, so that the rods 27, 28 extend upwardly from beneath the hood portion. The hood portion 42 is closed at the rear 44, and open at the front 45, and leads into the funnel portion 48.

Figure 6:
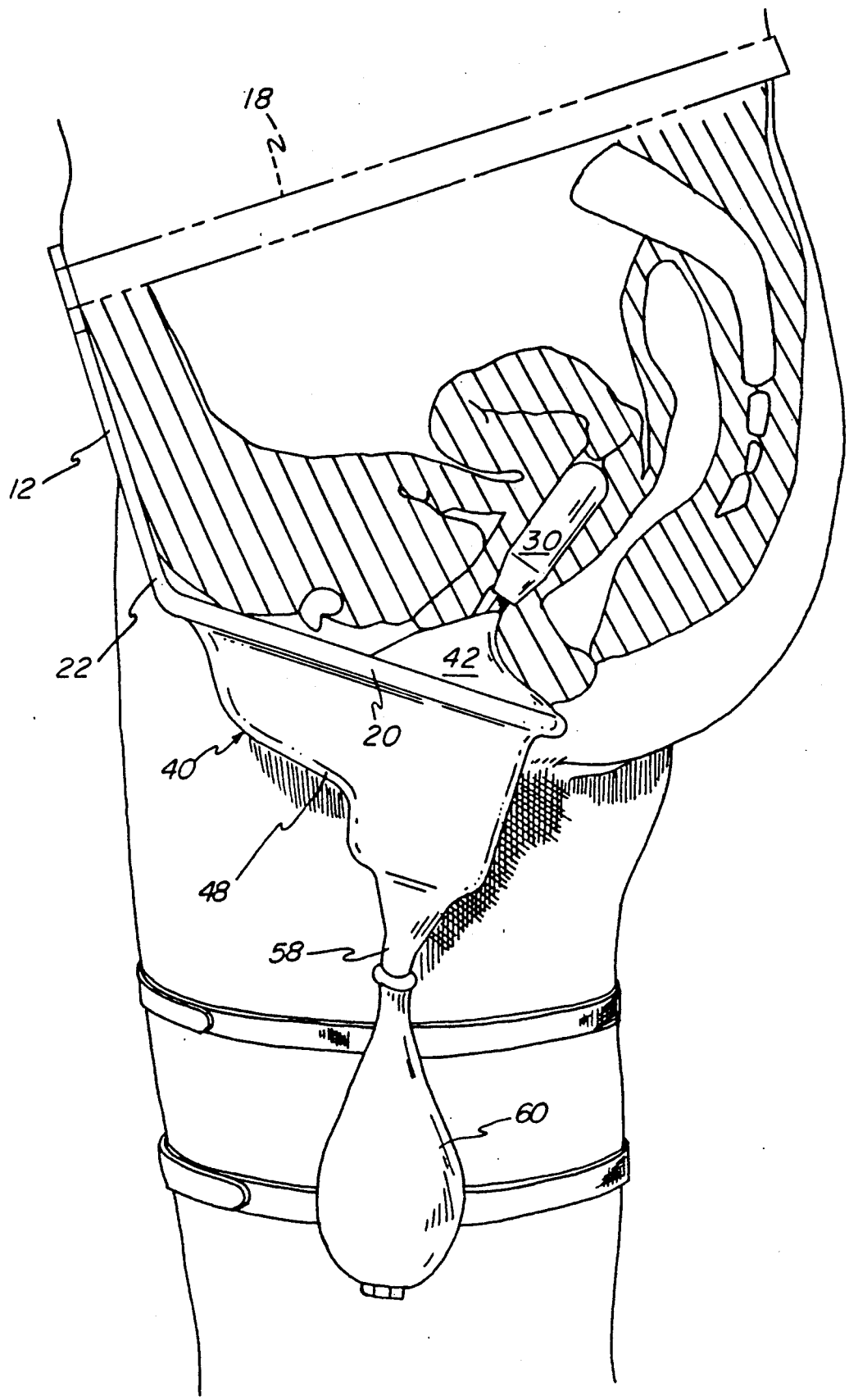
FIG. 6 illustrates the anatomical placement of the embodiment of FIG. 1.

The funnel portion 48 is integral with the hood portion, and molded about the body 20. It is also formed of a compliant and soft material, such as medical grade vinyl. The top 50 of the funnel portion 48 is formed by parallel side walls 52 and 53 which extend along the arms 22,24 to form a collection opening. The lower end 55 of the funnel portion 48 tapers downwardly into a collection nipple 58. A suitable tube (not shown) may be slipped over the end of the nipple 58 to lead to a convention thigh-attached collection bag 60 (FIG. 6), or the mouth of the bag may be received directly over the nipple.

The cylinder inserts 30, 31 may be removably attached to the ends of the rods, so that other sizes of inserts may be substituted, to provide a desired fit as required. The inserts are preferably formed of a medical grade PVC or rigid vinyl and may be removed from the end of rods 27, 28 such as for cleaning and/or replacement, as noted. The rods themselves extend a substantial axial distance into the inserts, and in appropriate circumstances patients have reported greater comfort by replacing the insert bulbs 30, 31 with a soft medical vinyl sleeve, slipped over the ends of the rods. Such a sleeve would be replaceable to maintain hygiene. Such a sleeve would be tubular with a closed end to receive the remote ends of the rods.

The appliance is easy to attach and use. The rods may be squeezed by the fingers of the patient to bring the flat sides of the inserts together for insertion into the vagina. The inserts (or the sleeve covering) will be slightly spread apart after insertion and will be urged against the anterior wall. The pad 12 may then be sprung up and over the pubis, and the belt attached. The major and minor vaginal lips are comfortably adjusted about the arms 22, 24. The apex of the hood portion forms a rounded prominence which rises with the body portion 25 form a soft hood and creates a sack to assist in the containment of exuding urine, and posterior seepage of urine is diverted into the funnel portion.

The spring action of the pliable rods 27, 28 tend to cause the inserts to rise and spread, to provide a support which gently pulls the hood 42 upward to a point where the hood tip is introduced into the lower portion of the vagina. In this manner a seal is formed which prevents posterior leakage, and tends to contain urine in the hood and collection cup 40. In the preceding embodiment, the urine which was collected by the combination hood and cup 40 is delivered by the nipple 58 to a remote container. However, as previously mentioned, it is desirable to use the appliance with patients who are confined to a chair or bed and where a collection funnel and collection bag is not feasible. The embodiment shown in FIGS. 7 through 11, respectively, has been designed particularly for such purpose, and the collection cup means is generally closed along the sides and at the bottom to provide an interior space for the retention of a fluid absorbing material, such as starch-containing polymeric compositions as described in the above-referenced U.S. Pat. Nos. 3,997,484 and 3,981,100.

The appliance 100 is retained in place with a support mechanism identical to that previously supplied by the appliance 10. Like reference numerals are applied to the drawings, and the description of the preferred embodiment of FIGS. 1 through 6, in connection with the insertion and retention mechanism, applies equally to the appliance 100.

The principal difference resides in the configuration of the collection cup means 40 identified in this embodiment as 40a. The bottom collection funnel portion is eliminated and is closed by a closed bottom wall 102. The anterior or front portion is provided with a closure flap 105, which may be open, as illustrated in the phantom view of FIG. 10, to provide access to the interior of the cup means 40. The flap may be closed or held shut by any suitable means, such as a snap or other gripping means, to retain the absorbent material and to provide access for its removal and replacement without the necessity of having to remove the appliance. Obviously, other means such as sliding or fasteners or the like may be employed for providing access to the interior of the collection cup 40a as necessary.

While the forms of apparatus herein described constitute preferred embodiments of this invention, it is to be understood that the invention is not limited to these precise forms of apparatus, and that changes may be made therein without departing form the scope of the invention which is defined in the appended claims.

What is claimed is:

1. A pubovaginal appliance for the collection of urine from women suffering from incontinence comprising a pad configured to engage a pubic region, a bifurcated support body attached to an end of said pad and defining a pair of spaced arm portions including means for extending from a location anterior to the vagina posteriorly along the contour of the perineum and terminating in a pair of flexible rods which are bent anteriorly and which terminate at distal ends, said rods diverging from each other with increasing distance from said arm portions, an enlarged vaginal insert carried on said distal end of each of said rods and proportioned to be received in the vaginal cavity, said rods biasing said inserts toward said pad to provide a self-holding force for said appliance between the pubis and vagina, and urine collection cup means carried by said body for enclosing the urethra and the sides of the vagina to collect urine from the urethra.

2. The appliance of claim 1 in which said inserts each have a shape in the general form of a cylinder, and in which said rods urge said inserts laterally from each other as well as toward said pad.

3. The appliance of claim 1 further including funnel means associated with said urine collection cup means for collecting urine and for delivery thereof to a container.

4. The appliance of claim 1 further comprising trap door means on said urine collection cup means providing access into the interior of said cup means to permit the insertion and removal of a urine absorbent material while said appliance is being worn with said support body extending along the contour of the perineum.

5. A pubovaginal appliance for the collection of urine from women suffering from incontinence comprising a pad configured to engage a pubic region, a support body means attached to an end of said pad for extending from a location anterior to the vagina posteriorly along the contour of the perineum and having means therein for defining an elongated opening adjacent to the perineum, said body further having a pair of insert support rods extending therefrom and carried on said body and extends anteriorly, an enlarged vaginal insert carried on a distal end of each of said rods and proportioned to be received in the vaginal cavity, said rods biasing said inserts anteriorly toward said pad to provide a self-holding force for said appliance between the pubis and vagina, a urine collection cup carried by said body at said opening and positioned to collect urine from the urethra, said urine collection cup having a hood which partially encloses said rods, said hood being closed at a posterior end thereof and attached peripherally to said urine collection cup and being open at a front end thereof to assist in the collection of urine into said urine collection cup, and container means connected to receive urine from said urine collection cup.

6. The appliance of claim 5 further comprising means on each of said inserts defining opposed flat surfaces which permit said inserts to abut against each other as a single unit for ease of insertion.

7. The appliance of claim 5 further comprising container means connected to receive urine from said urine collection cup.

8. The appliance of claim 5 further comprising means on said urine collection cup forming an openable and closable access panel for enabling insertion and removal therethrough of urine absorbent material from said cup when said support body is extending along the contour of the perineum.

* * * * *